(12) United States Patent
Akao

(10) Patent No.: US 11,605,963 B2
(45) Date of Patent: *Mar. 14, 2023

(54) POWER SUPPLY UNIT FOR AEROSOL INHALER AND CONTROL METHOD AND PROGRAM OF POWER SUPPLY UNIT FOR AEROSOL INHALER

(71) Applicant: JAPAN TOBACCO INC., Tokyo (JP)

(72) Inventor: Takeshi Akao, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/412,865

(22) Filed: Aug. 26, 2021

(65) Prior Publication Data

US 2021/0391737 A1 Dec. 16, 2021

Related U.S. Application Data

(63) Continuation of application No. 16/745,517, filed on Jan. 17, 2020, now Pat. No. 11,133,692.

(Continued)

(30) Foreign Application Priority Data

Feb. 28, 2019 (JP) .............................. JP2019-035994

(51) Int. Cl.
*H02J 7/00* (2006.01)
*A24F 40/90* (2020.01)
(Continued)

(52) U.S. Cl.
CPC ............ *H02J 7/0068* (2013.01); *A24F 40/40* (2020.01); *A24F 40/50* (2020.01); *A24F 40/51* (2020.01);
(Continued)

(58) Field of Classification Search
CPC ...................................................... H02J 7/0068
(Continued)

(56) References Cited

U.S. PATENT DOCUMENTS 5,166,596 A 11/1992 Goedken
11,133,692 B2 * 9/2021 Akao ...................... H02J 7/005
(Continued)

FOREIGN PATENT DOCUMENTS

CN 101546920 A 9/2009
CN 108652086 A 10/2018
(Continued)

OTHER PUBLICATIONS

Motification of Reasons for Refusal issued in Japanese Patent Application No. 2019-035994, dated Jul. 16, 2019 (6 pages).
(Continued)

*Primary Examiner* — Yalkew Fantu
(74) *Attorney, Agent, or Firm* — Osha Bergman Watanabe & Burton LLP

(57) ABSTRACT

A power supply unit for an aerosol inhaler includes: a case; a power supply that discharges power to a load for generating an aerosol from an aerosol generation source; a discharging terminal that connects the load to the power supply; a charging terminal that connects the power supply to an external power supply and is separated from the discharging terminal; a temperature measuring unit that measures temperature of the power supply; and a control device that controls an effective value of a first charging current to a value smaller than an effective value of a second charging current. The first charging current is supplied to the power supply when a measurement value of the temperature measuring unit is equal to or higher than a first threshold and the
(Continued)

second charging current is supplied to the power supply when the measurement value is lower than the first threshold.

12 Claims, 8 Drawing Sheets

Related U.S. Application Data

(60) Provisional application No. 62/793,551, filed on Jan. 17, 2019.

(51) Int. Cl.

| | | |
|---|---|---|
| *A24F 40/51* | (2020.01) | |
| *A24F 40/60* | (2020.01) | |
| *A61M 15/00* | (2006.01) | |
| *H05K 1/18* | (2006.01) | |
| *A24F 40/53* | (2020.01) | |
| *A24F 40/50* | (2020.01) | |
| *H05K 1/14* | (2006.01) | |
| *A24F 40/40* | (2020.01) | |
| *G05F 3/18* | (2006.01) | |
| *H01M 10/42* | (2006.01) | |
| *A24F 40/95* | (2020.01) | |
| *H02J 7/04* | (2006.01) | |
| *A61M 15/06* | (2006.01) | |
| *A24F 40/30* | (2020.01) | |

(52) U.S. Cl.
CPC .............. *A24F 40/53* (2020.01); *A24F 40/60* (2020.01); *A24F 40/90* (2020.01); *A24F 40/95* (2020.01); *A61M 15/009* (2013.01); *G05F 3/18* (2013.01); *H01M 10/425* (2013.01); *H02J 7/005* (2020.01); *H02J 7/007* (2013.01); *H02J 7/0042* (2013.01); *H02J 7/0045* (2013.01); *H02J 7/0063* (2013.01); *H02J 7/007194* (2020.01); *H02J 7/04* (2013.01); *H05K 1/14* (2013.01); *H05K 1/181* (2013.01); *A24F 40/30* (2020.01); *A61M 15/0003* (2014.02); *A61M 15/06* (2013.01); *A61M 2205/3653* (2013.01); *A61M 2205/50* (2013.01); *A61M 2205/8206* (2013.01); *A61M 2205/8237* (2013.01); *A61M 2205/8243* (2013.01); *H05K 2201/10015* (2013.01); *H05K 2201/10022* (2013.01); *H05K 2201/10174* (2013.01)

(58) Field of Classification Search
USPC ............................................................. 320/134
See application file for complete search history.

(56) References Cited

U.S. PATENT DOCUMENTS

| | | |
|---|---|---|
| 2008/0224667 A1 | 9/2008 | Tanaka et al. |
| 2009/0237142 A1 | 9/2009 | Matsuda et al. |
| 2015/0020831 A1* | 1/2015 | Weigensberg ......... A24F 40/50 131/329 |
| 2015/0173124 A1 | 6/2015 | Qiu |
| 2015/0237917 A1 | 8/2015 | Lord |
| 2015/0357839 A1 | 12/2015 | Cai et al. |
| 2017/0033568 A1 | 2/2017 | Holzherr |
| 2017/0049151 A1 | 2/2017 | Xue et al. |
| 2017/0238608 A1 | 8/2017 | Matsumoto et al. |
| 2017/0250552 A1 | 8/2017 | Liu |
| 2019/0252888 A1 | 8/2019 | Holzherr |
| 2020/0128883 A1* | 4/2020 | Yamada ................. A24F 40/53 |
| 2020/0128884 A1* | 4/2020 | Yamada ................. A61M 11/042 |
| 2020/0136415 A1* | 4/2020 | Akao .................... H02J 7/0068 |
| 2020/0212517 A1* | 7/2020 | Akao ..................... A24F 40/53 |

FOREIGN PATENT DOCUMENTS

| | | |
|---|---|---|
| JP | 2008-228492 A | 9/2008 |
| JP | 2009-219221 A | 9/2009 |
| JP | 2011-097728 A | 5/2011 |
| JP | 2017-079747 A | 5/2017 |
| JP | 2017-518733 A | 7/2017 |
| TW | 201707587 A | 3/2017 |
| WO | 2018/203044 A1 | 11/2018 |

OTHER PUBLICATIONS

Decision to Grant a Patent issued in corresponding Japanese Patent Application No. 2019-0359994 dated Dec. 17, 2019 (8 pages).
European Search Report issued in corresponding European Patent Application 20152297.6 dated May 12, 2020 (4 pages).
Office Action issued in corresponding Taiwanese Patent Application No. 109101545, dated Jul. 10, 2020 (10 pages).
Office Action issued in corresponding Chinese Application No. 202010052142.8 dated Nov. 2, 2022 (27 pages).

* cited by examiner

POWER SUPPLY UNIT FOR AEROSOL INHALER AND CONTROL METHOD AND PROGRAM OF POWER SUPPLY UNIT FOR AEROSOL INHALER

CROSS-REFERENCE TO RELATED APPLICATIONS

This is a Continuation Application of U.S. patent application Ser. No. 16/745,517 filed Jan. 17, 2020.

TECHNICAL FIELD

The present invention relates to a power supply unit for an aerosol inhaler, and a control method and program of a power supply unit for an aerosol inhaler.

BACKGROUND ART

There is available an aerosol inhaler that includes an aerosol generation source, a load for generating an aerosol from the aerosol generation source, a power supply able to discharge power to the load, and a control unit controlling the power supply (for example, see Patent Literatures 1 to 4).
[Patent Literature 1] US 2017/0250552 A1
[Patent Literature 2] US 2015/0173124 A1
[Patent Literature 3] JP-T-2017-518733
[Patent Literature 4] JP-A-2017-079747

Since an aerosol inhaler is frequently used, it is required to suppress deterioration of a power supply of the aerosol inhaler.

As a charging device for charging a power supply, a device which performs charging control according to the temperature of a power supply disclosed in Patent Literatures 3 and 4 is known.

For example, in the charging device, if the temperature of the power supply becomes high, the charging is ended to protect the power supply.

However, if the charging is ended early, the available time of an aerosol inhaler becomes shorter.

Therefore, convenience for a user is impaired.

In Patent Literatures 1 and 2, acquiring the temperature of a power supply is disclosed, however, any specific mode of charging control based on the acquired temperature is not disclosed.

In Patent Literatures 3 and 4, it is disclosed that when the temperature of the power supply is high, the charging is ended, however, any method for preventing the charging from being ended early is not disclosed.

An object of the present invention is to provide a power supply unit for an aerosol inhaler, and a control method and program of a power supply unit for an aerosol inhaler, making it possible to keep charging a power supply for as long as possible in order to extend the available time of an aerosol inhaler.

SUMMARY OF INVENTION

According to an aspect of the invention, there is provided a power supply unit for an aerosol inhaler, the power supply unit comprising: a power supply able to discharge power to a load for generating an aerosol from an aerosol generation source; a temperature measuring unit configured to measure temperature of the power supply; and a control device configured to control first power or a first amount of power to be supplied to the power supply in a case where a measurement value of the temperature measuring unit is equal to or higher than a first threshold, to a value smaller than second power or a second amount of power to be supplied to the power supply in a case where the measurement value is lower than the first threshold.

DESCRIPTION OF EMBODIMENTS

Figure 1:
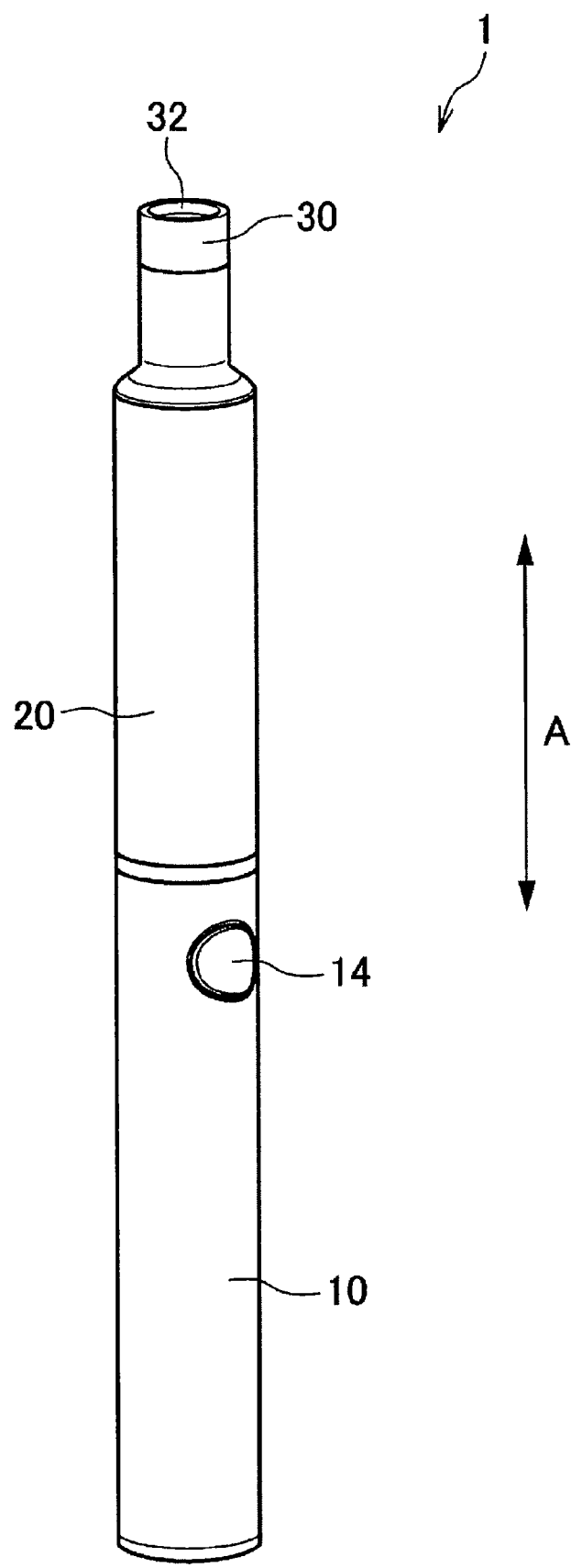
FIG. 1 is a perspective view of an aerosol inhaler equipped with a power supply unit of an embodiment of the present invention.
Figure 2:
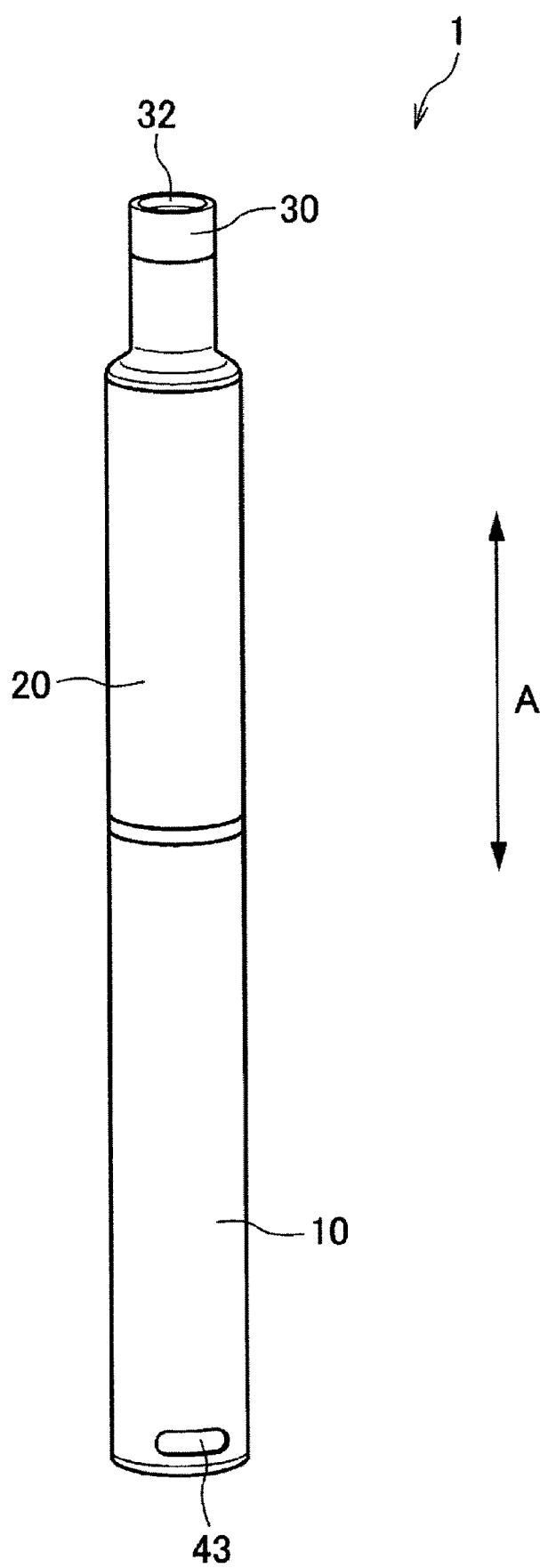
FIG. 2 is another perspective view of the aerosol inhaler of FIG. 1.

Hereinafter, a power supply unit for an aerosol inhaler according to an embodiment of the present invention will be described. First of all, an aerosol inhaler equipped with the power supply unit will be described with reference to FIG. 1 and FIG. 2.

(Aerosol Inhaler)

An aerosol inhaler 1 is a device for inhaling an aerosol containing a flavor without combustion, and has a rod shape extending along a certain direction (hereinafter, referred to as the longitudinal direction A). The aerosol inhaler 1 includes a power supply unit 10, a first cartridge 20, and a second cartridge 30 which are arranged in the order along the longitudinal direction A. The first cartridge 20 can be attached to and detached from the power supply unit 10. The second cartridge 30 can be attached to and detached from the first cartridge 20. In other words, the first cartridge 20 and the second cartridge 30 can be individually replaced.

(Power Supply Unit)

The power supply unit 10 of the present embodiment includes a power supply 12, a charging IC (Integrated Circuit) 55, an MCU (Micro Controller Unit) 50, a switch 19, a temperature sensor 17, various sensors, and so on inside a cylindrical power supply unit case 11, as shown in FIG. 3, FIG. 4, FIG. 5, and FIG. 6. As the MCU 50, an MCU whose shortest control cycle (the reciprocal of the maximum operation clock frequency) is longer than the shortest control cycle of the charging IC 55 is used.

The power supply 12 is a chargeable secondary battery, an electric double-layer capacitor, or the like, and is preferably a lithium-ion battery.

The temperature sensor 17 is configured, for example, with an temperature detection element whose resistance value changes according to temperature, specifically, an NTS (Negative Temperature Coefficient) thermistor. The temperature sensor 17 is for detecting the temperature of the power supply 12, and is disposed close to the power supply 12.

On a top part 11a of the power supply unit case 11 positioned on one end side in the longitudinal direction A (the first cartridge (20) side), a discharging terminal 41 is provided. The discharging terminal 41 is provided so as to protrude from the top surface of the top part 11a toward the first cartridge 20, and is configured to be able to be electrically connected to a load 21 of the first cartridge 20. Further, on a part of the top surface of the top part 11a in the vicinity of the discharging terminal 41, an air supply part 42 for supplying air to the load 21 of the first cartridge 20 is provided.

On a bottom part 11b of the power supply unit case 11 positioned on the other end side in the longitudinal direction A (the opposite side to the first cartridge 20), a charging terminal 43 able to be electrically connected to an external power supply is provided. The charging terminal 43 is provided on the side surface of the bottom part 11b, such that, for example, at least one of USB terminals, micro USB terminals, and lightning terminals (registered as a trade mark) can be connected thereto.

However, the charging terminal 43 may be a power receiving part able to receive power from an external power supply in a non-contact manner. In this case, the charging terminal 43 (the power receiving part) may be composed of a power receiving coil. The wireless power transfer system may be an electromagnetic induction type, or may be a magnetic resonance type. Also, the charging terminal 43 may be a power receiving part able to receive power from an external power supply without any contact point. As another example, the charging terminal 43 may be configured such that at least one of USB terminals, micro USB terminals, and lightning terminals can be connected thereto and the above-mentioned power receiving part is included therein.

On the side surface of the top part 11a of the power supply unit case 11, an operation unit 14 which the user can operate is provided so as to face the opposite side to the charging terminal 43. More specifically, the operation unit 14 and the charging terminal 43 are symmetric with respect to the point of intersection of a straight line connecting the operation unit 14 and the charging terminal 43 and the center line of the power supply unit 10 in the longitudinal direction A. The operation unit 14 is composed of a button type switch, a touch panel, or the like. In the vicinity of the operation unit 14, an inhalation sensor 15 for detecting puff actions are provided.

The charging IC 55 is disposed, for example, close to the charging terminal 43, and performs control to convert power which is input from an external power supply to the charging terminal 43 into charging power for the power supply 12 and supply the charging power to the power supply 12.

Figure 5:
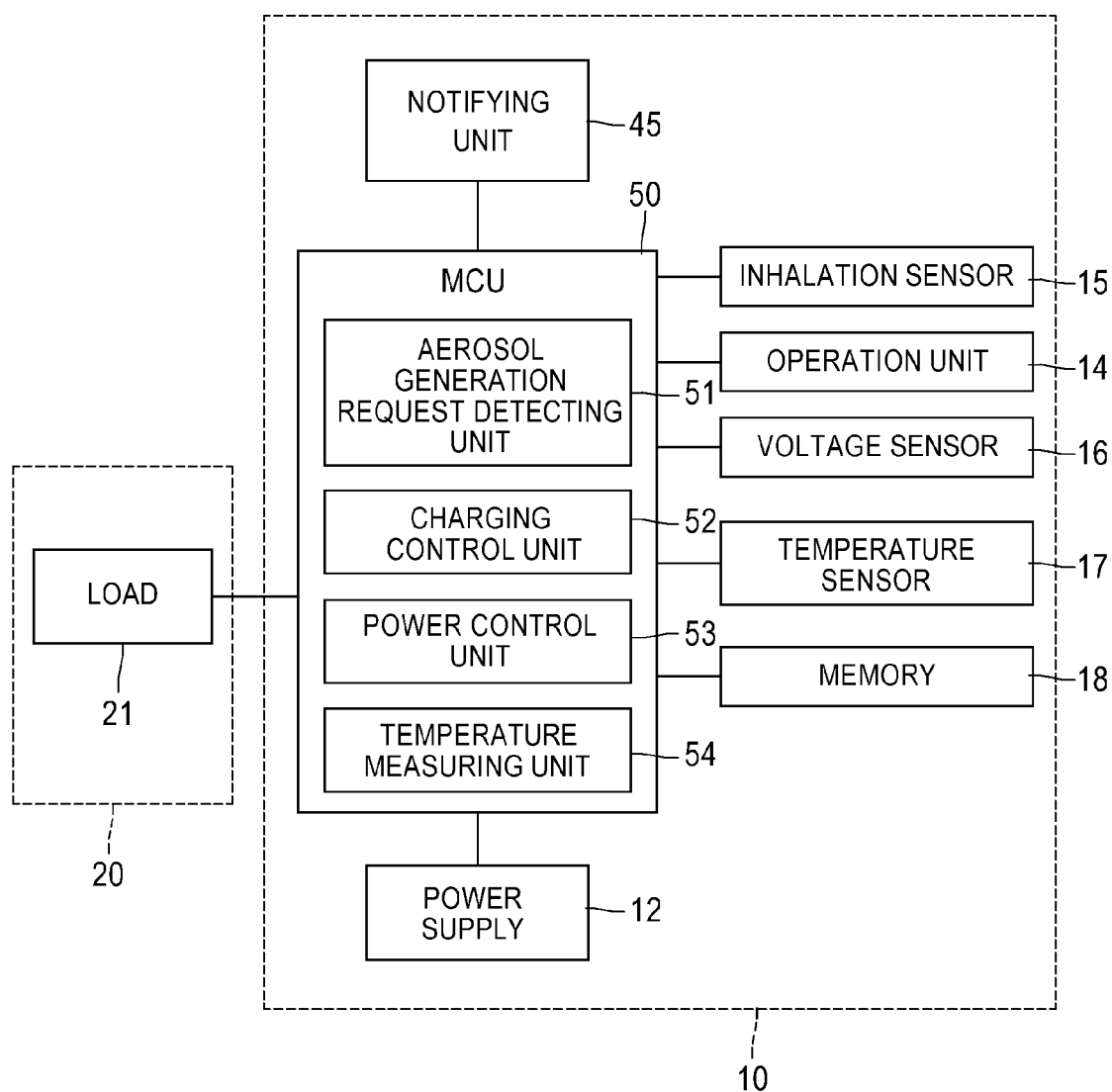
FIG. 5 is a block diagram illustrating the main part configuration of the power supply unit in the aerosol inhaler of FIG. 1.

The MCU 50 is connected to various sensor devices such as the inhalation sensor 15 for detecting puff (inhaling) actions, a voltage sensor 16 for measuring the power-supply voltage of the power supply 12, and a temperature sensor 17 provided to measure the temperature of the power supply 12, the operation unit 14, a notifying unit 45, and a memory 18 for storing the number of puff actions, the time for which power has been applied to the load 21, and so on, as shown in FIG. 5, and performs a variety of control on the aerosol inhaler 1. Specifically, the MCU 50 is mainly composed of a processor, and further includes storage media such as a RAM (Random Access Memory) necessary for the operation of the processor and a ROM (Read Only Memory) for storing a variety of information. In this specification, the processor is more specifically an electric circuit configured by combining circuit elements such as semiconductor elements.

Also, in the power supply unit case 11, an air intake (not shown in the drawings) for taking in air is formed. The air intake may be formed around the operation unit 14, or may be formed around the charging terminal 43.

(First Cartridge)

Figure 3:
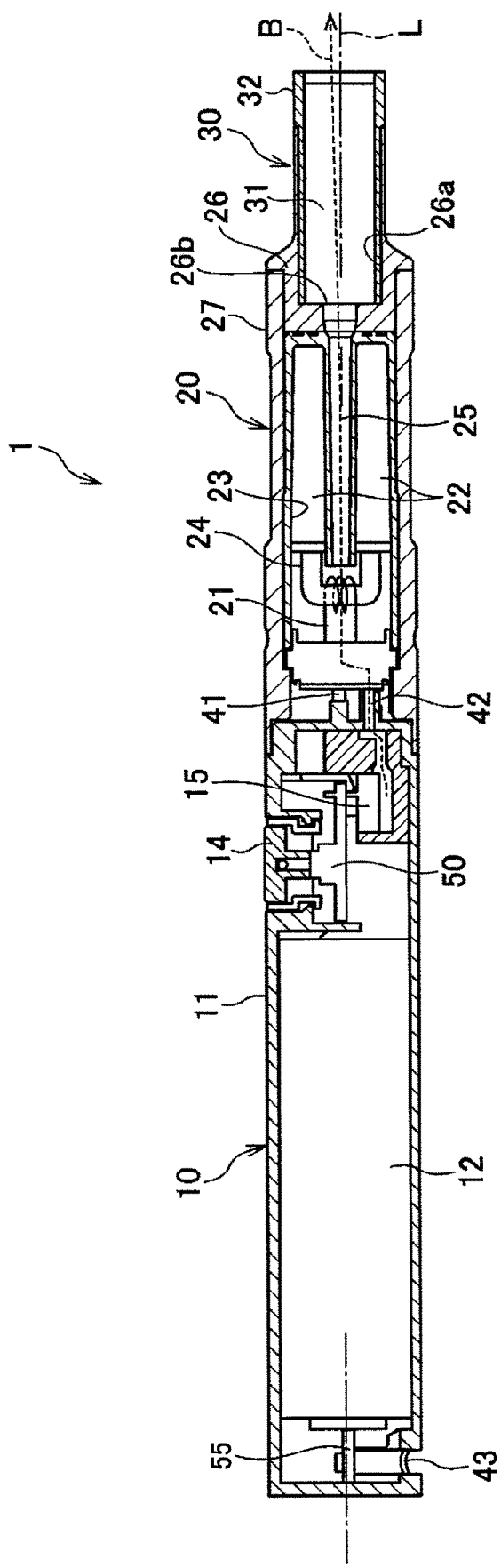
FIG. 3 is a cross-sectional view of the aerosol inhaler of FIG. 1.
Figure 4:
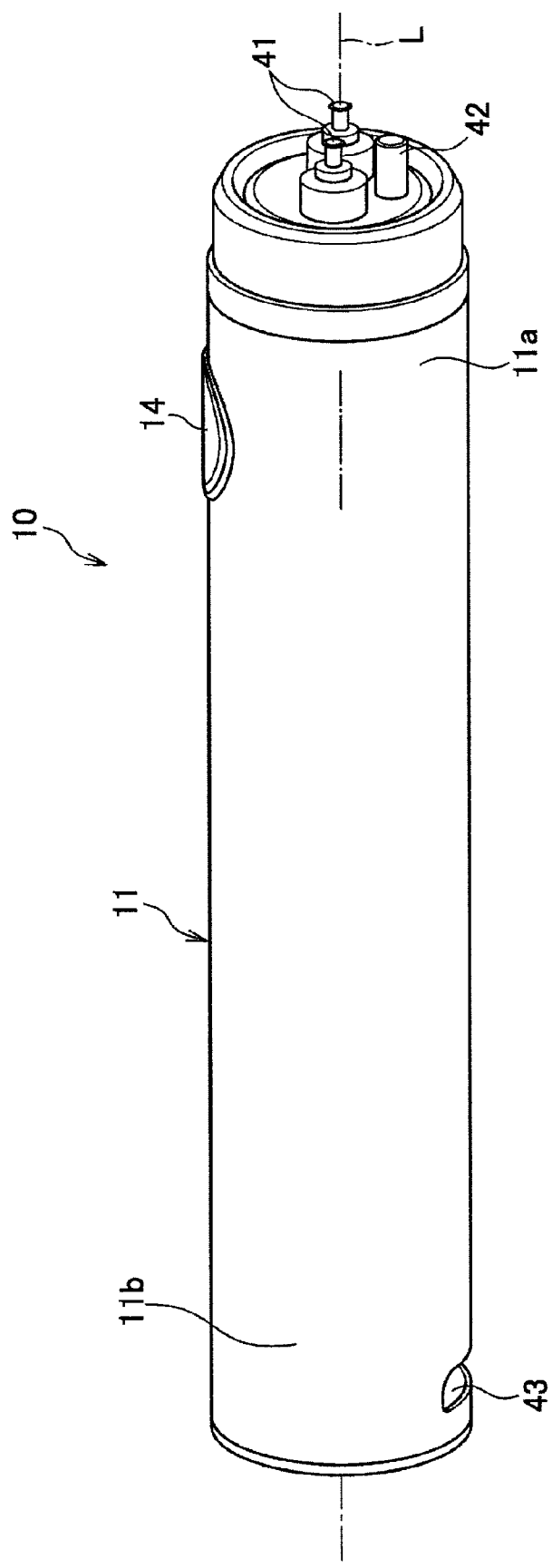
FIG. 4 is a perspective view of the power supply unit in the aerosol inhaler of FIG. 1.

As shown in FIG. 3, the first cartridge 20 includes a reservoir 23 for storing an aerosol source 22, the electric load 21 for atomizing the aerosol source 22, a wick 24 for drawing the aerosol source from the reservoir 23 toward the load 21, an aerosol channel 25 for an aerosol generated by atomizing the aerosol source 22 to flow toward the second cartridge 30, an end cap 26 for storing a part of the second cartridge 30, inside a cylindrical cartridge case 27.

The reservoir 23 is formed so as to surround the aerosol channel 25, and holds the aerosol source 22. In the reservoir 23, a porous member such as a resin web or cotton may be stored, and the porous member may be impregnated with the aerosol source 22. The aerosol source 22 includes a liquid such as glycerin, propylene glycol, or water.

The wick 24 is a liquid holding member for drawing the aerosol source 22 from the reservoir 23 toward the load 21 using capillarity, and is configured with, for example, glass fiber, a porous ceramic, or the like.

The load 21 atomizes the aerosol source 22, without combustion, by power which is supplied from the power supply 12 through the discharging terminal 41. The load 21 is configured with a heating wire wound with a predetermined pitch (a coil). However, the load 21 needs only to be an element capable of atomizing the aerosol source 22, thereby generating an aerosol, and is, for example, a heating element or an ultrasonic wave generator. Examples of the heating element include a heating resistor, a ceramic heater, an induction heating type heater, and so on.

The aerosol channel 25 is provided on the downstream side of the load 21 on the center line L of the power supply unit 10.

The end cap 26 includes a cartridge storage part 26a for storing a part of the second cartridge 30, and a connecting passage 26b for connecting the aerosol channel 25 and the cartridge storage part 26a.

(Second Cartridge)

The second cartridge 30 holds a flavor source 31. An end part of the second cartridge 30 on the first cartridge (20) side is stored in the cartridge storage part 26a provided in the end cap 26 of the first cartridge 20, so as to be able to be removed. Another end part of the second cartridge 30 on the opposite side to the first cartridge (20) side is configured as an inhalation port 32 for the user. However, the inhalation port 32 does not necessarily need to be configured integrally with the second cartridge 30 so as not to be separable from the second cartridge, and may be configured to be able to be attached to and detached from the second cartridge 30. If the inhalation port 32 is configured separately from the power supply unit 10 and the first cartridge 20 as described above, it is possible to keep the inhalation port 32 sanitary.

The second cartridge 30 adds a flavor to the aerosol generated by atomizing the aerosol source 22 by the load 21, by passing the aerosol through the flavor source 31. As a raw material piece which constitutes the flavor source, a compact made by forming shredded tobacco or a tobacco raw material into a grain shape can be used. The flavor source 31 may be configured with plants (such as mint, herbal medicines, herbs) other than tobacco. To the flavor source 31, a flavoring agent such as menthol may be added.

The aerosol inhaler 1 of the present embodiment can generate an aerosol containing the flavor by the aerosol source 22, the flavor source 31, and the load 21. In other words, the aerosol source 22 and the flavor source 31 constitute an aerosol generation source for generating an aerosol.

The aerosol generation source in the aerosol inhaler 1 is a part which the user can replace to use. For this part, for example, one first cartridge 20 and one or more (for example, five) second cartridges 30 can be provided as one set to the user.

The configuration of the aerosol generation source which can be used in the aerosol inhaler 1 is not limited to the configuration in which the aerosol source 22 and the flavor source 31 are configured separately, and may be a configuration in which the aerosol source 22 and the flavor source 31 are formed integrally, a configuration in which the flavor source 31 is omitted and the aerosol source 22 contains a substance which can be contained in the flavor source 31, a configuration in which the aerosol source 22 contains a medical substance or the like instead of the flavor source 31, or the like.

For an aerosol inhaler 1 including an aerosol generation source configured by integrally forming an aerosol source 22 and a flavor source 31, for example, one or more (for example, 20) aerosol generation sources may be provided as one set to the user.

In the case of an aerosol inhaler 1 including only an aerosol source 22 as an aerosol generation source, for example, one or more (for example, 20) aerosol generation sources may be provided as one set to the user.

In the aerosol inhaler 1 configured as described above, as shown by an arrow B in FIG. 3, air entering from the intake (not shown in the drawings) formed in the power supply unit case 11 passes through the air supply part 42, and passes near the load 21 of the first cartridge 20. The load 21 atomizes the aerosol source 22 drawn from the reservoir 23 by the wick 24. The aerosol generated by atomizing flows through the aerosol channel 25 together with the air entering from the intake, and is supplied to the second cartridge 30 through the connecting passage 26b. The aerosol supplied to the second cartridge 30 passes through the flavor source 31, whereby the flavor is added, and is supplied to the inhalation port 32.

Also, in the aerosol inhaler 1, the notifying unit 45 for notifying a variety of information is provided (see FIG. 5). The notifying unit 45 may be configured with a light emitting element, or may be configured with a vibrating element, or may be configured with a sound output element. The notifying unit 45 may be a combination of two or more elements of light emitting elements, vibrating elements, and sound output elements. The notifying unit 45 may be provided in any one of the power supply unit 10, the first cartridge 20, and the second cartridge 30; however, it is preferable that the notifying unit be provided in the power supply unit 10. For example, the area around the operation unit 14 is configured to have translucency to permit light which is emitted by light emitting elements such as LEDs to pass through.

(Electric Circuit)

Now, the details of the electric circuit of the power supply unit 10 will be described with reference to FIG. 6.

The power supply unit 10 includes, as main components, the power supply 12, the temperature sensor 17, the switch 19, a positive electrode side discharging terminal 41a and a negative electrode side discharging terminal 41b which constitute the discharging terminal 41, a positive electrode side charging terminal 43a and a negative electrode side charging terminal 43b which constitute the charging terminal 43, the MCU 50, the charging IC 55, resistors 61 and 62 composed of elements having resistance values, such as resistive elements or transistors, switches 63 and 64 composed of transistors such as MOSFETs, or the like, and a resistive element 65.

In the present embodiment, an example using "BQ24040DSQT" made by Texas Instruments Inc. as the charging IC 55 is shown; however, the charging IC is not limited thereto. The charging IC 55 has a plurality of pins including an IN pin (shown by "IN" in FIG. 6), an OUT pin (shown by "OUT" in FIG. 6), a TS pin (shown by "TS" in FIG. 6), a #CHG pin (shown by "#CHG" in FIG. 6), and an EP pin (shown by "EP" in FIG. 6), as pins for electrical connection with the outside. However, it should be noted that in the present embodiment, only main pins of pins which the charging IC 55 has are disclosed.

Also, in the present embodiment, an example using "PIC16F18346" made by Microchip Technology Inc. as the MCU 50 is shown; however, the MCU is not limited thereto. The MCU 50 has a plurality of pins including a Vdd pin (shown by "Vdd" in FIG. 6), an RA4 pin (shown by "RA4" in FIG. 6), a #RC3 pin (shown by "#RC3" in FIG. 6), a #RC4 pin (shown by "#RC4" in FIG. 6), a #RC5 pin (shown by "#RC5" in FIG. 6), a RB7 pin (shown by "RB7" in FIG. 6), and an EP pin (shown by "EP" in FIG. 6), as pins for electrical connection with the outside. However, it should be noted that in the present embodiment, only main pins of pins which the MCU 50 has are disclosed.

The IN pin of the charging IC 55 is an input terminal for power which is supplied from the charging terminal 43 (power for generating charging power). The IN pin of the charging IC 55 is connected to the positive electrode side charging terminal 43a.

The OUT pin of the charging IC 55 is an output terminal for the charging power generated by the charging IC 55. To the OUT pin of the charging IC 55, a power source line 60V is connected. This power source line 60V is connected to the positive electrode side discharging terminal 41a through the switch 19.

The EP pin of the charging IC 55 is a ground terminal. The EP pin of the charging IC 55 is connected to a ground line 60E which connects the negative electrode side charging terminal 43b and the negative electrode side discharging terminal 41b.

The #CHG pin of the charging IC 55 is a terminal for outputting charging state information indicating that charging is being performed, charging is stopped, or charging has been completed. The #CHG pin of the charging IC 55 is connected to the #RC5 pin of the MCU 50.

The TS pin of the charging IC 55 is a terminal for inputting a voltage value which is applied to a resistor which is connected thereto (a voltage value according to the resistance value of the corresponding resistor). From the voltage value input to the TS pin, the resistance value of the resistor which is connected to the TS pin (in other words, the temperature of the corresponding resistor) can be detected. When a thermistor is used as a resistor which is connected to the TS pin, it is possible to detect the temperature of the resistor which is connected to the TS pin, from a voltage value input to the TS pin.

The charging IC 55 has a function of controlling charging voltage to be output from the OUT pin, based on a voltage value which is input to the TS pin. Specifically, the charging IC 55 outputs a first charging voltage from the OUT pin, in the case where the temperature based on the voltage value which is input to the TS pin is lower than a threshold TH1, and outputs a second charging voltage lower than the first charging voltage, in the case where the temperature is equal to or higher than the threshold TH1 and is lower than a threshold TH2, and performs control to prevent charging voltage from being output from the OUT pin, i.e. to stop charging, in the case where the temperature is equal to or higher than the threshold TH2. The threshold TH1 is, for example, 40° C., and the threshold TH2 is, for example, 45° C.

The voltage value of the resistor which is connected to the TS pin in the case where the temperature of the resistor becomes the threshold TH1 is denoted by Vmax, and the voltage value of the resistor which is connected to the TS pin in the case where the temperature of the resistor becomes the threshold TH2 is denoted by Vmin. In the case where the resistor which is connected to the TS pin is an NTC thermistor, as the temperature of the resistor rises, the resistance value of the resistor decreases. Therefore, the relation of Vmax>Vmin is established. This should be noted. Based on the above-mentioned definition, the charging IC 55 outputs the second charging voltage from the OUT pin, in the case where the voltage value which is input to the TS pin is included in a predetermined range larger than Vmin and equal to or smaller than Vmax, and outputs the first charging voltage from the OUT pin, in the case where the voltage value which is input to the TS pin exceeds Vmax, and stops charging in the case where the voltage value which is input to the TS pin is smaller than Vmin.

To the TS pin of the charging IC 55 of the present embodiment, one end of the resistor 61 is connected. The other end of the resistor 61 is connected to the ground line 60E. Also, to the TS pin of the charging IC 55, one end of the switch 63 is connected. To the other end of the switch 63, one end of the resistor 62 is connected. The other end of the resistor 62 is connected to the ground line 60E.

Each of the resistor 61 and the resistor 62 has a predetermined fixed resistance value. The resistor 61, and the series circuit of the switch 63 and the resistor 62 are connected to the TS pin in parallel. Therefore, when the switch 63 is off (when it is nonconductive), a voltage value V1 on the resistor 61 which is caused by current flowing from the TS pin to the resistor 61 is input to the TS pin.

The voltage value V1 becomes a constant value since the resistance value of the resistor 61 is a fixed value. The resistance value of the resistor 61 is determined in advance such that the voltage value V1 becomes an arbitrary value in the above-mentioned performed range (larger than Vmin and equal to or smaller than Vmax). It is preferable to determine the resistance value of the resistor 61 in advance such that in the case where the median value of the predetermined range is Vc, the voltage value V1 becomes a value closer to Vmax than to Vc. In this case, even if the voltage value which is input to the TS pin changes due to noise or errors, it is possible to keep charging of the charging IC 55 on the power supply 12. As described above, the resistance value of the resistor 61 is determined such that the voltage value V1 becomes a value for outputting the second charging voltage from the OUT pin of the charging IC 55. The resistance value of the resistor 61 is specifically 4.7 kω.

Also, the resistance value of the resistor 62 is set to a value sufficiently smaller than the resistance value of the resistor 61. Therefore, when the switch 63 is on (when it is conductive), current preferentially flows from the TS pin to the resistor 62, and a voltage value V2 on the resistor 62 which is caused by the current is input to the TS pin.

This voltage value V2 becomes a constant value since the resistance value of the resistor 62 is a fixed value. The resistance value of the resistor 62 is determined in advance such that the voltage value V2 becomes an arbitrary value smaller than Vmin. As described above, the resistance value of the resistor 62 is determined in advance such that the voltage value V2 becomes a value for stopping charging of the charging IC 55 on the power supply 12.

However, the resistor 62 is not essential, and can be omitted. In other words, the other end of the switch 63 may be connected directly to the ground line 60E. In this case, when the switch 63 is on, the TS pin is grounded. Therefore, it is possible to make the voltage value to be input to the TS pin, smaller than Vmin. Therefore, by turning on the switch 63, it is possible to stop charging of the charging IC 55 on the power supply 12. Also, by omitting the resistor 62, it is possible to reduce the cost and the weight.

The positive electrode side of power supply 12 is connected to the power source line 60V, and the negative electrode side thereof is connected to the ground line 60E. Therefore, the power supply can be charged with the charging voltage output from the OUT pin of the charging IC 55 to the power source line 60V.

The Vdd pin of the MCU 50 is a power supply terminal, and is connected to the power source line 60V.

The EP pin of the MCU 50 is a ground terminal, and is connected to the ground line 60E.

The RA4 pin of the MCU 50 is connected to the switch 63, and is used as a terminal for performing control to turn on and off the switch 63.

The RB7 pin of the MCU 50 is connected to the switch 19, and is used as a terminal for performing control to turn on and off the switch 19.

The #RC5 pin of the MCU 50 is used as a terminal for receiving the charging state of the charging IC 55 from the #CHG pin of the charging IC 55.

The #RC4 pin of the MCU 50 is connected to the switch 64, and is used as a terminal for performing control to turn on and off the switch 64. One end of the switch 64 is connected to the power source line 60V, and the other end thereof is connected to one end of the resistive element 65. The other end of the resistive element 65 is connected to one end of the NTC thermistor constituting the temperature sensor 17. The other end of the NTC thermistor constituting the temperature sensor 17 is connected to the ground line 60E.

The #RC3 pin of the MCU 50 is used as a terminal for detecting the temperature of the power supply 12. The #RC3 pin of the MCU 50 is connected to the connection point between the resistive element 65 and the temperature sensor 17.

When the switch 64 is on (when it is conductive), the voltage on the power source line 60V is divided by the resistive element 65 and the temperature sensor 17, and the voltage value which is applied to the temperature sensor 17 is input to the #RC3 pin of the MCU 50. The MCU 50 has a function of measuring the temperature of the power supply 12 based on the voltage value which is input to the #RC3 pin, as will be described below.

Meanwhile, when the switch 64 is off (when it is nonconductive), voltage is not supplied to the temperature sensor 17. Therefore, in this case, the MCU 50 changes to the state where it cannot acquire the temperature of the power supply 12.

The switch 19 is composed of, for example, a semiconductor element such as a MOSFET, and is turned on and off under the control of the MCU 50.

Figure 6:
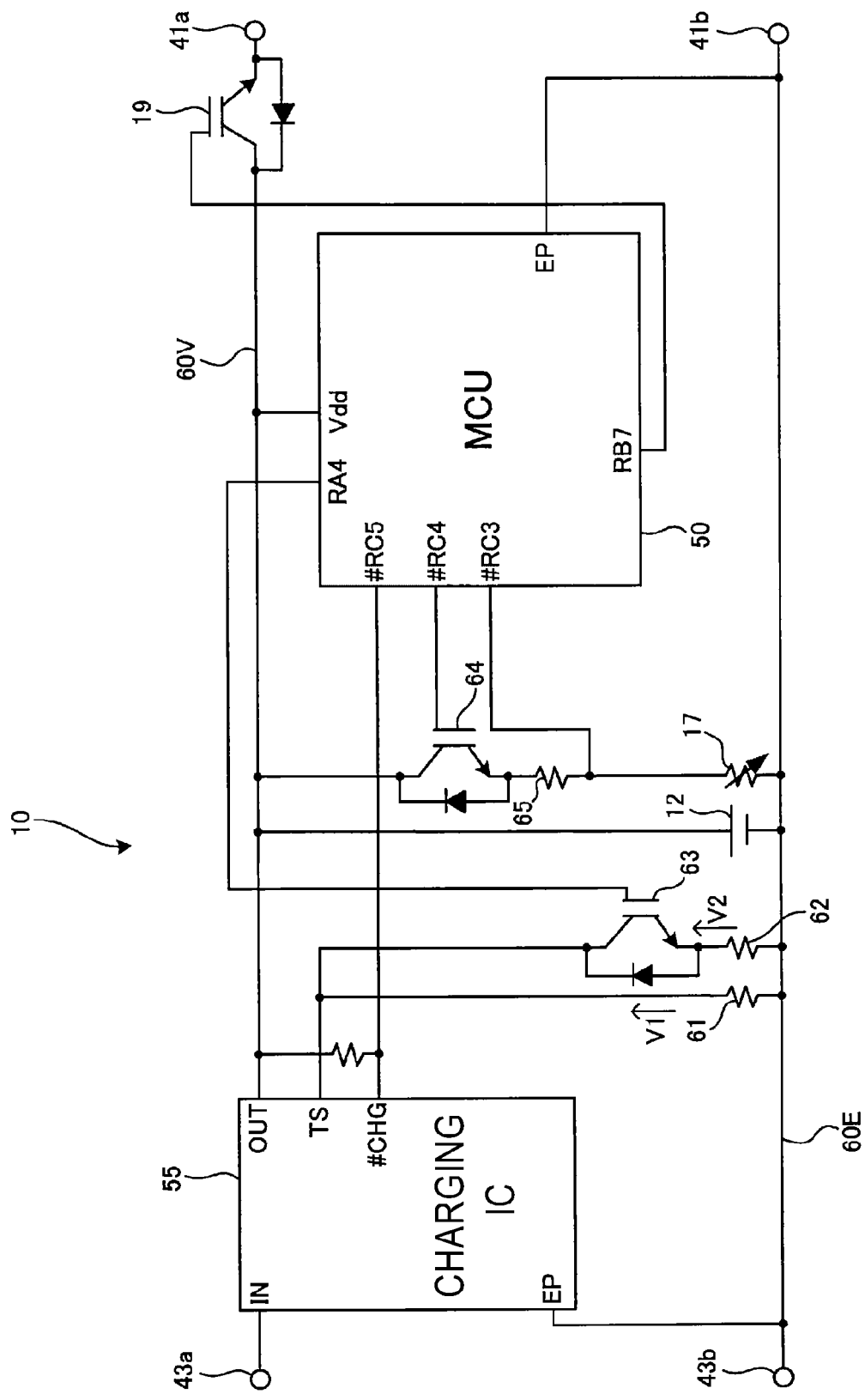
FIG. 6 is a schematic diagram illustrating the main part circuit configuration of the power supply unit in the aerosol inhaler of FIG. 1.

In the electric circuit of the power supply unit 10 shown in FIG. 6, the switch 19 is provided between the positive electrode side of the power supply 12 and the positive electrode side discharging terminal 41a. Instead of this so-called plus control type, the switch 19 may be a minus control type which is provided between the negative electrode side discharging terminal 41b and the negative electrode side of the power supply 12.

(MCU)

Now, the configuration of the MCU 50 will be described in more detail.

As shown in FIG. 5, the MCU 50 includes an aerosol generation request detecting unit 51, a charging control unit 52, a power control unit 53, and a temperature measuring unit 54, as functional blocks which are realized by executing a program stored in the ROM by a processor.

The aerosol generation request detecting unit 51 detects a request for aerosol generation based on the output result of the inhalation sensor 15. The inhalation sensor 15 is configured to output the value of a variation in the pressure in the power supply unit 10 (the internal pressure) caused by inhalation of the user through the inhalation port 32. The inhalation sensor 15 is, for example, a pressure sensor for outputting an output value (for example, a voltage value or a current value) according to the internal pressure which varies according to the flow rate of air which is sucked from the intake (not shown in the drawings) toward the inhalation port 32 (i.e. a puff action of the user). The inhalation sensor 15 may be configured with a capacitor microphone or the like.

The power control unit 53 controls discharging of the power supply 12 through the discharging terminal 41 by switching on and off the switch 19, if the aerosol generation request detecting unit 51 detects the request for aerosol generation.

The power control unit 53 performs control such that the amount of aerosol which is generated by atomizing the aerosol source by the load 21 falls in a desired range, i.e. such that power or the amount of power which is supplied from the power supply 12 to the load 21 falls in a predetermined range. Specifically, the power control unit 53 controls switching on and off of the switch 19 by, for example, PWM (Pulse Width Modulation) control. Alternatively, the power control unit 53 may control switching on and off of the switch 19 by PFM (Pulse Frequency Modulation) control.

After supply of power to the load 21 starts in order to generate an aerosol, if a predetermined period passes, the power control unit 53 stops supply of power from the power supply 12 to the load 21. In other words, even while the user is actually performing a puff action, if the puff period exceeds a certain period, the power control unit 53 stops supply of power from the power supply 12 to the load 21. The certain period is determined to suppress variation in user's puff period.

By control of the power control unit 53, the current which flows in the load 21 during one puff action becomes substantially a constant value which is determined according to substantially constant effective voltage which is supplied to the load 21 by PWM control, and the resistance values of the discharging terminal 41 and the load 21. In the aerosol inhaler 1 of the present embodiment, when the user inhales an aerosol using one unused second cartridge 30, the cumulative time for which power can be supplied to the load 21 is controlled to a maximum of, for example, 120 seconds. To this end, it is possible to obtain the maximum amount of power required to empty (use up) one second cartridge 30 in advance.

The temperature measuring unit 54 measures the temperature of the power supply 12, based on the voltage value of the temperature sensor 17 which is input to the #RC3 pin.

The charging control unit 52 controls the charging voltage to be supplied to the power supply 12, by performing control to turn on and off the switch 63, based on the temperature of the power supply 12 measured by the temperature measuring unit 54.

Figure 7:
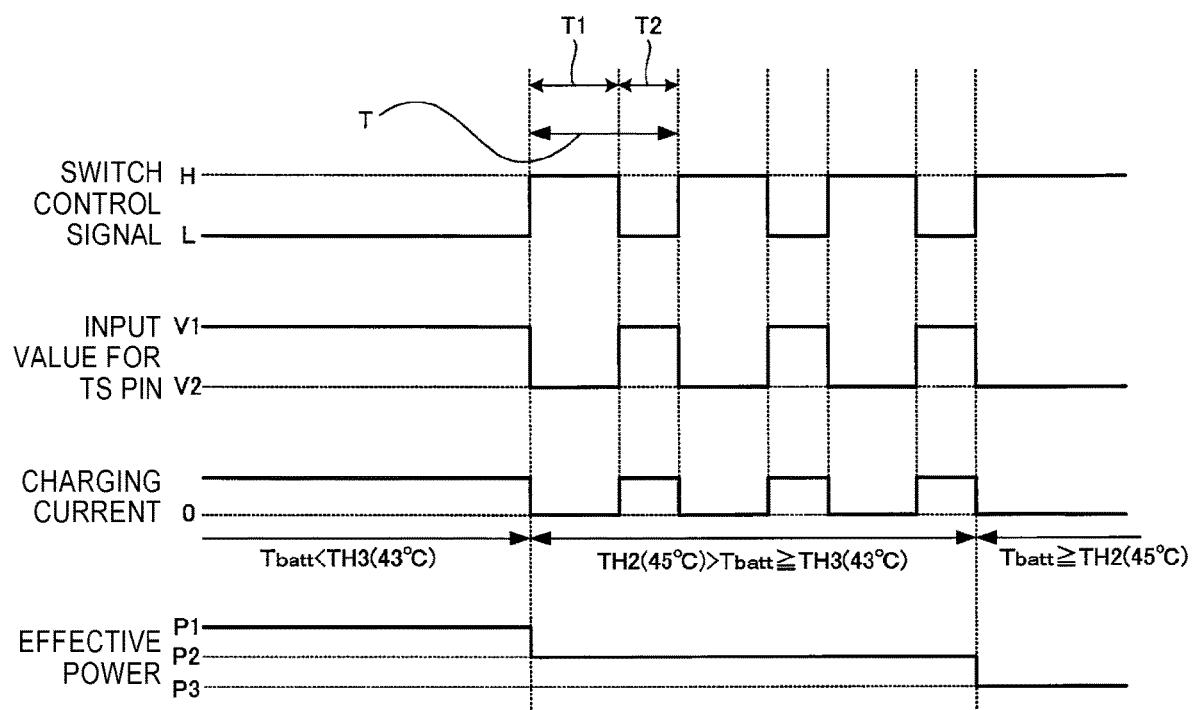
FIG. 7 is a timing chart illustrating the control content of a charging control unit shown in FIG. 5.

FIG. 7 is the timing chart illustrating the control content of the charging control unit 52. As shown in FIG. 7, if the temperature Tbatt of the power supply 12 becomes equal to or higher than the threshold TH2 (in the example of FIG. 7, 45° C.), the charging control unit 52 maintains a switch control signal to be input to the switch 63, at the high level, thereby maintaining the switch 63 in the ON state. When the switch 63 is maintained in the ON state, the voltage value V2 for stopping charging is continuously input to the TS pin of the charging IC 55. Therefore, charging of the power supply 12 is stopped, and the charging current for the power supply 12 becomes zero.

In the case where the temperature Tbatt of the power supply 12 is lower than a threshold TH3, the charging control unit 52 maintains the switch control signal to be input to the switch 63, at the low level, thereby maintaining the switch 63 in the OFF state. The threshold TH3 is a value smaller than the threshold TH2 and larger than the threshold TH1 (for example, 40° C.), and in the example of FIG. 7, the threshold TH3 is 43° C. When the switch 63 is maintained in the OFF state, the voltage value V1 for supplying the second charging voltage is continuously input to the TS pin of the charging IC 55. Therefore, the second charging voltage is supplied to the power supply 12, and the charging current for the power supply 12 becomes a predetermined value larger than zero.

In the case where the temperature Tbatt of the power supply 12 is in a range equal to or larger than the threshold TH3 and smaller than the threshold TH2, the charging control unit 52 performs control to switch the switch control signal to be input to the switch 63 between the low level and the high level, thereby switching the switch 63.

As shown in FIG. 7, on the assumption that the switching cycle is a predetermined unit time T, for a time T1 which is a part of the unit time T, the charging control unit 52 performs control to maintain the switch 63 in the ON state, and for a time T2 of the unit time T other than the time T1, the charging control unit performs control to maintain the switch 63 in the OFF state. Since the switch 63 is switched under the above-described control, the charging current for the power supply 12 alternately changes between the predetermined value and zero.

When the ratio of the time T1 (the time for which control is performed to maintain the ON state) to the unit time T is defined as the duty ratio, in the state where the temperature Tbatt is lower than the threshold TH3, control using 0% as the duty ratio is performed, and in the state where the temperature Tbatt is equal to or higher than the threshold TH3 and is lower than the threshold TH2, control using a duty ratio larger than 0% and smaller than 100% (in the example of FIG. 7, the duty ratio of 60%) is performed, and in the state where the temperature Tbatt is higher than the threshold TH2, control using 100% as the duty ratio is performed.

By the way, if the switch 63 is controlled to be in the ON state, the charging current for the power supply 12 becomes zero. Therefore, it should be noted that the value obtained by subtracting the duty ratio of the switch 63 from 100% becomes the duty ratio of the charging current. For example, when the duty ratio of the switch 63 is 0%, the duty ratio of the charging current becomes 100%, and when the duty ratio of the switch 63 is 60%, the duty ratio of the charging current becomes 40%. In the following description, unless otherwise noted, duty ratios indicates the duty ratios of the switch 63.

In periods when control using the duty ratio of 0% is performed, effective power (the average work amount per unit time T of the charging current) P1 which is supplied to the power supply 12 becomes a maximum value. In periods when control using the duty ratio larger than 0% and smaller than 100% is performed, effective power P2 which is supplied to the power supply 12 is a value lower than the effective power P1. In periods when control using the duty ratio of 100% is performed, effective power P3 which is supplied to the power supply 12 is a value (a minimum value) lower than the effective power P2. Also, the effective power P2 is a value obtained by subtracting the duty ratio from 100% and multiplying the effective power P1 by the difference (in the example of FIG. 7, the value of 0.4 times the effective power P1).

For periods when control using a duty ratio larger than 0% and smaller than 100% needs to be performed, as the duty ratio, a sufficiently small value is set in advance such that the temperature Tbatt of the power supply 12 does not reach the threshold TH2. As this duty ratio, a value equal to or larger than 50% is preferable, and a value equal to or larger than 60% is more preferable. By setting such a value, it is possible to sufficiently reduce the possibility that the temperature Tbatt might reach the threshold TH2.

Alternatively, the charging control unit 52 may control the amount of power to be supplied to the power supply 12 for a predetermined period (for example, the unit time T), instead of effective power. In the case where the power supply unit 10 has a DC-to-DC converter and a smoothing capacitor, the charging control unit 52 may control the amount of power to be supplied to the power supply 12, instead of effective power. In this case, for example, in the predetermined period, the charging control unit 52 decreases the magnitude of the charging current while continuously supplying the charging current to the power supply 12, thereby reducing the amount of power to be supplied to the power supply 12 for the predetermined period. In other words, the charging control unit controls the charging current for the power supply 12 to any one of a predetermined value, an intermediate value smaller than the predetermined value, and zero. In this case, in a state where the charging current has been controlled to the predetermined value, it is possible to make the amount of power to a maximum value, and in a state where the charging current has been controlled to an intermediate value, it is possible to make the amount of power to the value smaller than the maximum value, and in a state where the charging current has been controlled to zero, it is possible to make the amount of power to a minimum value.

The duty ratio may be a fixed value, or may be a variable changing according to the amount of change in the temperature Tbatt. For example, in the case where a rise per unit time T in the temperature Tbatt is equal to or larger than a predetermined value, the duty ratio is set to be larger than that in the case where a rise per unit time is smaller than the predetermined value. In this way, it is possible to reduce the possibility that the temperature of the power supply 12 might reach the threshold TH2, and extend the duration of charging of the power supply 12.

Also, it is preferable that a value which is obtained by subtracting the threshold TH3 from the threshold TH2 should be equal to or larger than the absolute values of errors of the temperature measuring unit 54 in measuring the temperature of the power supply 12. An error of the temperature measuring unit 54 in measuring the temperature of the power supply 12 means an error including an error in the amount of change in the resistance value of the temperature sensor 17 according to temperature and an error in the voltage value which is input to the #RC3 pin. It is preferable that such measurement errors should include gain errors, offset errors, and hysteresis errors of the temperature sensor 17. Such measurement errors are about between −2° C. and 2° C.

The MCU 50 includes a notification control unit, besides the above-mentioned functional blocks. The notification control unit controls the notifying unit 45 such that the notifying unit notifies a variety of information. For example, the notification control unit controls the notifying unit 45 in response to detection of the timing to replace the second cartridge 30, such that the notifying unit notifies the timing to replace the second cartridge 30. The notification control unit detects and notifies the timing to replace the second cartridge 30, based on the cumulative number of puff actions or the cumulative time for which power has been supplied to the load 21, stored in the memory 18. The notification control unit is not limited to notification of the timing to replace the second cartridge 30, and may notify the timing to replace the first cartridge 20, the timing to replace the power supply 12, the timing to charge the power supply 12, and so on.

In the state where one unused second cartridge 30 is set, if a predetermined number of puff actions are performed, or if the cumulative time for which power has been applied to the load 21 due to puff actions reaches a predetermined value (for example, 120 seconds), the notification control unit determines that the second cartridge 30 is used up (i.e. the remaining amount is zero or the second cartridge is empty), and notifies the timing to replace the second cartridge 30.

Also, in the case of determining that all of the second cartridges 30 included in one set are used up, the notification control unit may determine that one first cartridge 20 included in the single set is used up (i.e. the remaining amount is zero or the first cartridge is empty), and notify the timing to replace the first cartridge 20.

(Power Supply Charging Operation)

Figure 8:
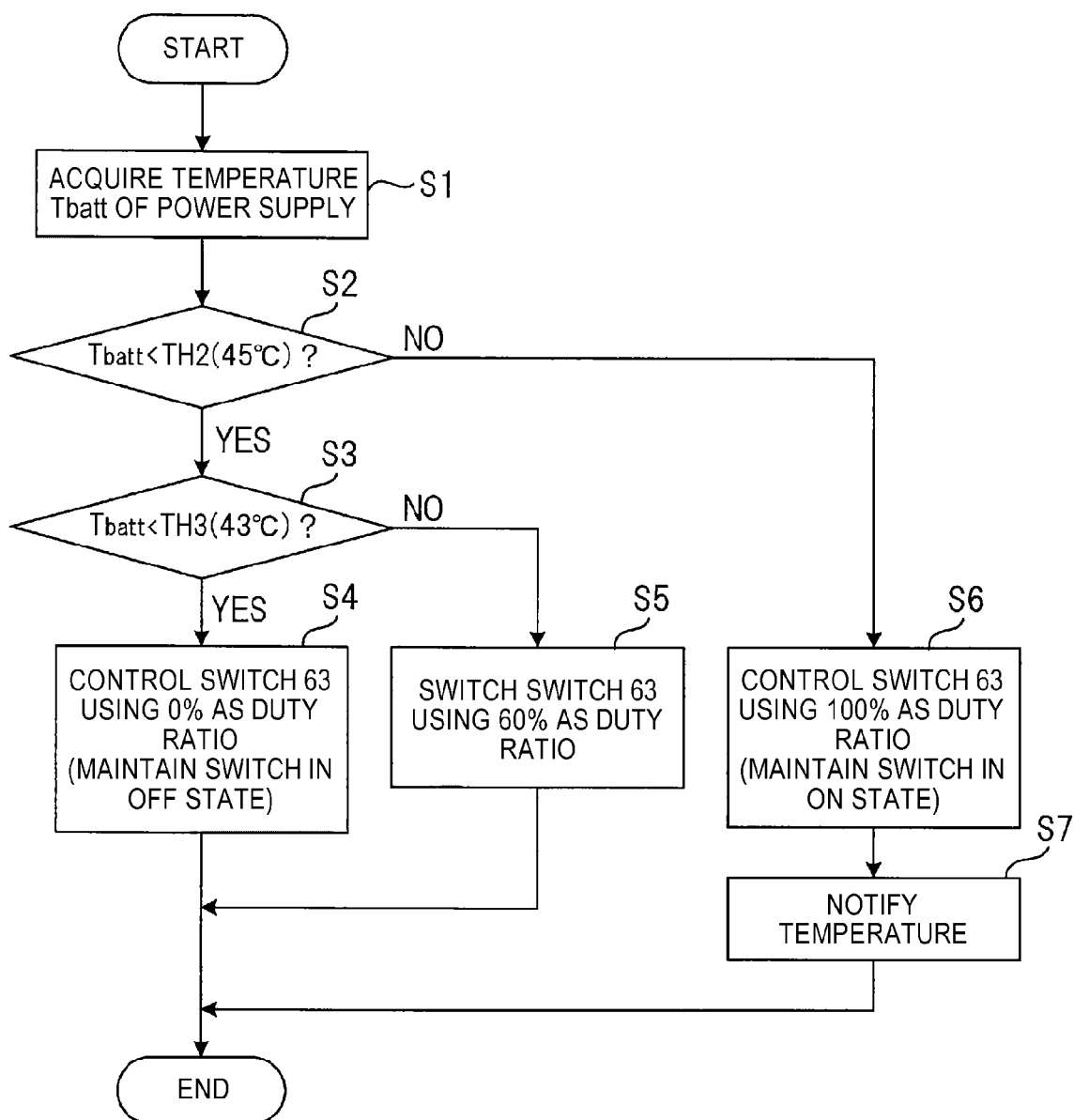
FIG. 8 is a flow chart for explaining the operation of the aerosol inhaler of FIG. 1 during charging of the power supply.

The operation of the aerosol inhaler 1 having the above-described configuration during charging of the power supply 12 will be described with reference to the flow chart of FIG. 8.

If a charging cable is connected to the charging terminal 43, and this charging cable is connected to an external power supply, a charging start signal is input from the #CHG pin of the charging IC 55 to the #RC5 pin of the MCU 50. Also, in a state before the charging start signal is input to the #RC5 pin of the MCU 50, the switch 63 and the switch 64 are off. In other words, if charging is started, the voltage value V1 according to the resistance value of the resistor 61 is input to the TS pin of the charging IC 55, and the power supply 12 is charged with the second charging voltage.

After the switch control signal is input to the #RC5 pin of the MCU 50, the MCU 50 regularly measures the temperature of the power supply 12. Specifically, the MCU 50 acquires the temperature of the power supply 12 in a cycle longer than the shortest control cycle of the power supply unit (preferably, at intervals of the same time as the above-mentioned unit time T), or at a frequency lower than the maximum operation frequency of the power supply unit, or at an operation clock frequency smaller than the maximum operation clock frequency. When a timing to acquire the temperature of the power supply 12 comes, the MCU 50 turns on the switch 64, and acquires the temperature Tbatt of the power supply 12 based on the voltage value which is input to the #RC3 pin, and turns off the switch 64 (STEP 51).

Then, the MCU 50 determines whether the acquired temperature Tbatt is lower than the threshold TH2, or not (STEP S2). If the temperature Tbatt is equal to or higher than the threshold TH2 ("NO" in STEP S2), the MCU 50 maintains the switch 63 in the ON state, i.e. it performs control using the duty ratio of 100% (STEP S6). According to this control, the voltage value V2 according to the resistance value of the resistor 62 is input to the TS pin of the charging IC 55. Then, the charging IC 55 stops supply of the charging voltage to the power supply 12.

After STEP S6, the MCU 50 notifies the charging IC 55 that the temperature of the power supply 12 has reached a protection temperature (STEP S7). If the charging IC 55 receives this notification, it outputs a charging stop signal from the #CHG pin. Then, the MCU 50 receives this signal, and returns the switch 63 to the OFF state. However, the order of STEP S6 and STEP S7 may be reversed, or STEP S6 and STEP S7 may be performed at the same time.

In the case where the temperature Tbatt is lower than the threshold TH2 ("YES" in STEP S2), the MCU 50 determines whether the temperature Tbatt is lower than the threshold TH3 (STEP S3). If the temperature Tbatt is lower than the threshold TH3 ("YES" in STEP S3), the MCU 50 maintains the switch 63 in the OFF state, i.e. it performs control using 0% as the duty ratio (STEP S4).

In the case where the temperature Tbatt is equal to or higher than the threshold TH3 ("NO" in STEP S3), the MCU 50 controls switching of the switch 63, for example, using 60% as the duty ratio (STEP S5). After STEP S4 and STEP S5, if the next temperature acquisition timing comes, the processing returns to STEP 51.

As described above, according to the power supply unit 10 of FIG. 6, in the case where the measurement value of the temperature of the power supply 12 becomes equal to or higher than the threshold TH3, effective power which is supplied to the power supply 12 becomes lower than that in the case where the temperature Tbatt is lower than the threshold TH3. Therefore, it is possible to reduce the possibility that the temperature of the power supply 12 might reach the threshold TH2, and it is possible to extend the time for which it is possible to continuously charge the power supply 12. As a result, it is possible to extend the available time of the aerosol inhaler 1.

Also, according to the power supply unit 10 of FIG. 6, in the case where the measurement value of the temperature of the power supply 12 is equal to or higher than the threshold TH2, charging of the power supply 12 is stopped. Therefore, it is possible to protect the power supply 12.

Also, according to the power supply unit 10 of FIG. 6, in the state where the temperature of the power supply 12 is lower than the threshold TH3, the charging IC 55 charges the power supply 12 with the second charging voltage lower than the first charging voltage which is the highest charging voltage which the charging IC can output. As described above, it becomes possible to continuously charge the power supply 12 with a low charging voltage. Therefore, it becomes possible to suppress deterioration of the power supply 12.

Also, according to the power supply unit 10 of FIG. 6, it is possible to suppress effective power to be supplied to the power supply 12 by controlling switching of the switch 63 while making it possible to charge the power supply 12 with a low charging voltage as described above. Therefore, even in the case using an inexpensive charging IC 55, it is possible to perform high-accuracy charging control capable of restraining the temperature of the power supply 12 from rising.

Also, according to the power supply unit 10 of FIG. 6, even in the case of using a charging IC 55 which needs a variable resistor to be connected to the TS pin when it is used, control to charge the power supply 12 with only a low charging voltage becomes possible. Therefore, it is not necessary to newly design a charging IC for generating a low charging voltage, and it is possible to reduce the manufacturing cost of the power supply unit 10.

By the way, in the power supply unit 10 of FIG. 6, since the resistance value of the resistor which is connected to the TS pin of the charging IC 55 is fixed, it is not possible to detect the temperature of the power supply 12 by the charging IC 55. However, the MCU 50 acquires the temperature of the power supply 12, and controls charging of the power supply 12 based on the acquired temperature. Therefore, it is possible to extend the duration of charging of the power supply 12, and prevent deterioration of the power supply 12 from being caused by a rise in the temperature.

Also, the MCU 50 acquires the temperature of the power supply 12 in a cycle longer than the shortest control cycle of the power supply unit. Therefore, the temperature of the power supply 12 is not acquired at an excessive frequency, and it is possible to reduce the power consumption. Also, it is possible to use calculation resources of the MCU 50 for other purposes.

Also, the MCU 50 can perform switching between a state where the temperature of the power supply 12 can be acquired and a state where the temperature of the power supply 12 cannot be acquired, by controlling switching of the switch 64. Since acquisition of the temperature becomes possible by easy control using the switch 64, it is possible to suppress the manufacturing cost. Also, since the temperature of the power supply 12 can be acquired only at timings when it is required, it is possible to reduce the power consumption.

In the electric circuit of FIG. 6 described above, the ground line 60E is a grounded wiring line; however, it needs only to be a wiring line having the lowest potential (a main negative bus line) in the power supply unit 10, and may not be a grounded wiring line.

In this specification, at least the following inventions (1) to (19) are disclosed. Moreover, although the corresponding constituent elements and the like in the embodiments described above are shown in parentheses, it is not limited thereto.

(1) A power supply unit for an aerosol inhaler, the power supply unit comprising:

a power supply (the power supply 12) able to discharge power to a load (the load 21) for generating an aerosol from an aerosol generation source;

a temperature measuring unit (the temperature measuring unit 54) configured to measure temperature of the power supply; and a control device (the MCU 50) configured to control first power (the effective power P2) or a first amount of power to be supplied to the power supply in a case where a measurement value of the temperature measuring unit is equal to or higher than a first threshold (the threshold TH3), to a value smaller than second power (the effective power P1) or a second amount of power to be supplied to the power supply in a case where the measurement value is lower than the first threshold.

According to (1), in the case where the measurement value of the temperature of the power supply is equal to or higher than the first threshold, the power or the amount of the power to be supplied to the power supply decreases. Therefore, it is possible to restrain the temperature of the power supply from rising, and it is possible to extend the time for it is possible to continuously charge the power supply 12. As a result, it is possible to extend the available time of the aerosol inhaler.

(2) The power supply unit according to (1), wherein in a case where the measurement value is equal to or higher than a second threshold (the threshold TH2) larger than the first threshold, the control device stops charging of the power supply.

According to (2), even in the case where the charging of the power supply is performed with low power or a small amount of power, if the measurement value of the temperature of the power supply becomes equal to or higher than the second threshold, it is possible to stop the charging of the power supply, so it is possible to protect the power supply.

(3) The power supply unit according to (1) or (2), wherein the first threshold is lower than 45° C.

According to (3), before the temperature of the power supply reaches 45° C. at which deterioration of the power supply is feared, it is possible to reduce power or the amount of power. Therefore, it is possible to prevent deterioration of the power supply.

(4) The power supply unit according to any one of (1) to (3), wherein the control device controls the first power or the first amount of power to 50% or less of the second power or the second amount of power.

According to (4), it is possible to effectively restrain the temperature of the power supply from rising.

(5) The power supply unit according to (4), wherein the control device controls the first power or the first amount of power to 40% or less of the second power or the second amount of power.

According to (5), it is possible to more effectively restrain the temperature of the power supply from rising.

(6) The power supply unit according to (1), wherein in a case where the measurement value is equal to or higher than a second threshold (the threshold TH2) larger than the first threshold, the control device stops charging of the power supply, and in a case where the measurement value is equal to or higher than the first threshold and is lower than the second threshold, the control device controls the first power or the first amount of power such that the measurement value does not become equal to or higher than the second threshold.

According to (6), it is possible to prevent the temperature of the power supply from reaching the second threshold. Therefore, it is possible to reduce the possibility that charging of the power supply might be stopped, and it is possible to keep charging for as long as possible.

(7) The power supply unit according to (1), wherein in a case where the measurement value is equal to or higher than a second threshold (the threshold TH2) larger than the first threshold, the control device stops charging of the power supply, and a value which is obtained by subtracting the first threshold from the second threshold is equal to or larger than an absolute value of an error of the temperature measuring unit in measuring the temperature.

According to (7), even in the case where whether the real temperature is the second threshold or not is unclear due to existence of a measurement error, when the measurement value becomes equal to or higher than the first threshold, i.e. at least before the real temperature exceeds the second threshold, it is possible to reduce the power or the amount of power. Therefore, it is possible to prevent the temperature of the power supply from exceeding the second threshold, and it is possible to keep charging for as long as possible.

(8) The power supply unit according to (1), wherein the first threshold is 43° C. or lower, and the control device controls the first power or the first amount of power to 40% or less of the second power or the second amount of power.

According to (8), it is possible to reduce the power or the amount of power before the temperature of the power supply reaches 45° C. at which deterioration of the power supply is feared. Therefore, it is possible to prevent deterioration of the power supply.

(9) The power supply unit according to any one of (1) to (8), further comprising:

a charger (the charging IC 55) configured to convert power which is input, into charging power for the power supply, wherein, among the charger and the control device, only the charging device includes the temperature measuring unit.

According to (9), since the temperature of the power supply can be measured by the control device generally having higher processing performance than chargers have, it is possible to accurately acquire the temperature at high frequency, and it becomes possible to perform high-accuracy control on charging and discharging, using the acquired temperature.

(10) The power supply unit according to (9), wherein the control device performs control on switching between a state where the temperature of the power supply can be acquired and a state where the temperature of the power supply cannot be acquired.

According to (10), since the temperature of the power supply can be acquired at timings when the temperature is required, it is possible to reduce the power consumption. Also, it is possible to use calculation resources of the control device for other purposes. Further, it is possible to improve the accuracy of control using the temperature of the power supply.

(11) The power supply unit according to (9) or (10), wherein the charger includes an information input part (the TS pin) and is configured to be able to supply one of a first charging voltage and a second charging voltage lower than the first charging voltage to the power supply, based on an input value which is input from the information input part, a fixed value (the voltage value V1) which is predetermined as one input value can be input to the information input part, and the fixed value is a value for supplying the second charging voltage to the power supply.

According to (11), in a state where the fixed value is being input to the information input part, it is possible to charge the power supply with the second charging voltage lower than the first charging voltage. For example, by realizing a state where the fixed value is continuously input to the information input part, it becomes possible to continuously charge the power supply with a low charging voltage, and it becomes possible to suppress deterioration of the power supply.

(12) The power supply unit according to (11), further comprising:

a switch (the switch 63) able to perform switching between a state where the fixed value is input to the information input part and a state where the fixed value is not input to the information input part, wherein the control device controls power to be supplied to the power supply, by controlling switching on and off of the switch.

According to (12), it is possible to input values other than the fixed value to the information input part. For example, by turning on the switch, it is possible to perform charging with the second charging voltage such that the first power or the first amount of power is supplied to the power supply, and by turning off the switch, it is possible to stop charging with the second charging voltage. Therefore, it becomes possible to supply the second power or the second amount of power smaller than the first power or the first amount of power, by alternately and repeatedly turning on and off the switch.

(13) The power supply unit according to (12), wherein in the state where the fixed value is not input to the information input part, the switch causes the charger to input a value (the voltage value V2) for stopping charging of the power supply, to the information input part.

According to (13), by turning on the switch, it is possible to perform charging with the second charging voltage such that the first power or the first amount of power is supplied to the power supply, and by turning off the switch, it is possible to stop charging with the second charging voltage. Therefore, it becomes possible to supply the second power or the second amount of power smaller than the first power or the first amount of power, by alternately and repeatedly turning on and off the switch. Also, in the case where the temperature of the power supply is such high that protection of the power supply is required, it is possible to input the value for stopping charging of the power supply to the information input part, thereby protecting the power supply.

(14) The power supply unit for an aerosol inhaler according to (12) or (13), wherein the input value is a value related to voltage to be applied to a resistor which is connected to the information input part, the power supply unit includes a fixed resistor (the resistor 61) having a fixed resistance value and connected to the information input part, the switch is provided between the information input part and a main negative bus line or a ground line (the ground line 60E), and the information input part and the main negative bus line or the ground line are directly connected by the switch, whereby the fixed value is not input to the information input part.

According to (14), since the information input part and either the main negative bus line or the ground line are directly connected, it is possible to make the voltage-related values to be input to the information input part, into sufficiently small values. In the case of using, as the charger, one having a function of stopping charging if a value which is input to the information input part becomes smaller than a threshold, in the corresponding state, it is possible to stop the charger from charging, so it is possible to protect the power supply.

(15) A power supply unit for an aerosol inhaler, the power supply unit comprising:

a power supply (the power supply 12) able to discharge power to a load (load 21) for generating an aerosol from an aerosol generation source;

a charger (the charging IC 55) configured to convert power which is input, into charging power for the power supply; and a control device (the MCU 50) configured to perform first control for stopping the charger from supplying power to the power supply and second control for making the charger supply power to the power supply, wherein the control device controls a ratio (the duty ratio) of a period when the first control is performed and a period when the second control is performed in a predetermined unit time (the unit time T).

According to (15), by only controlling the ratio of the period when the first control is performed and the period when the second control in the predetermined unit time, it is possible to control effective power to be supplied to the power supply. Therefore, even in the case of using an inexpensive charger, it is possible to perform high-accuracy charging control. For example, by controlling the above-mentioned ratio according to the temperature of the power supply, it becomes possible to restrain the temperature of the power supply from rising, and it is possible to keep charging the power supply for as long as possible.

(16) A control method of a power supply unit for an aerosol inhaler, the control method comprising:

a temperature measuring step of measuring temperature of a power supply (the power supply 12) able to discharge power to a load (the load 21) for generating an aerosol from an aerosol generation source; and a step of controlling first power or a first amount of power to be supplied to the power supply in a case where a measurement value of the temperature is equal to or higher than a first threshold, to a value smaller than second power or a second amount of power to be supplied to the power supply in a case where the measurement value is lower than the first threshold.

(17) A control program of a power supply unit for an aerosol inhaler for making a computer perform:

a temperature measuring step of measuring temperature of a power supply (the power supply 12) able to discharge power to a load (the load 21) for generating an aerosol from an aerosol generation source; and a step of controlling first power or a first amount of power to be supplied to the power supply in a case where a measurement value of the temperature is equal to or higher than a first threshold, to a value smaller than second power or a second amount of power to be supplied to the power supply in a case where the measurement value is lower than the first threshold.

(18) A control method of a power supply unit for an aerosol inhaler, the power supply unit including a power supply (the power supply 12) able to discharge power to a load (load 21) for generating an aerosol from an aerosol generation source, and a charger (the charging IC 55) configured to convert power which is input, into charging power for the power supply, the control method comprising:

a control step of performing first control for stopping the charger from supplying power to the power supply and second control for making the charger supply power to the power supply, wherein the control step controls a ratio (the duty ratio) of a period when the first control is performed and a period when the second control is performed in a predetermined unit time (the unit time T).

(19) A control program of a power supply unit for an aerosol inhaler, the power supply unit including a power supply (the power supply 12) able to discharge power to a load (load 21) for generating an aerosol from an aerosol generation source, and a charger (the charging IC 55) configured to convert power which is input, into charging power for the power supply, the control program for making a computer perform:

a control step of performing first control for stopping the charger from supplying power to the power supply and second control for making the charger supply power to the power supply, wherein the control step controls a ratio (the duty ratio) of a period when the first control is performed and a period when the second control is performed in a predetermined unit time (the unit time T).

What is claimed is:

1. A power supply unit for an aerosol inhaler, the power supply unit comprising:
   a case;
   a power supply which is able to discharge power to a load for generating an aerosol from an aerosol generation source and which is stored in the case;
   a discharging terminal configured to connect the load to the power supply;
   a charging terminal configured to connect the power supply to an external power supply and to be separate from the discharging terminal;
   a temperature measuring unit stored in the case to measure temperature of the power supply; and
   a control device configured to control an effective value of a first charging current to a value smaller than an effective value of a second charging current, wherein the first charging current is supplied to the power supply in a case where a measurement value of the temperature measuring unit is equal to or higher than a first threshold and the second charging current is supplied to the power supply in a case where the measurement value is lower than the first threshold.

2. The power supply unit according to claim 1, wherein the temperature measuring unit is stored in the case so as to be close to the power supply.

3. The power supply unit according to claim 1, wherein in a case where the measurement value is equal to or higher than a second threshold larger than the first threshold, the control device stops charging of the power supply.

4. The power supply unit according to claim 1, wherein the first threshold is lower than 45° C.

5. The power supply unit according to claim 1, wherein the control device controls first power or a first amount of power that is supplied to the power supply in a case where the measurement value is equal to or higher than the first threshold to 50% or less of second power or a second amount of power that is supplied to the power supply in a case where the measurement value is lower than the first threshold.

6. The power supply unit according to claim 5, wherein the control device controls the first power or the first amount of power to 40% or less of the second power or the second amount of power.

7. The power supply unit according to claim 1, wherein in a case where the measurement value is equal to or higher than a second threshold larger than the first threshold, the control device stops charging of the power supply, and
in a case where the measurement value is equal to or higher than the first threshold and is lower than the second threshold, the control device controls first power or a first amount of power that is supplied to the power supply in a case where the measurement value is equal to or higher than the first threshold such that the measurement value does not become equal to or higher than the second threshold.

8. The power supply unit according to claim 1, wherein the first threshold is 43° C. or lower, and
the control device controls first power or a first amount of power that is supplied to the power supply in a case where the measurement value is equal to or higher than the first threshold to 40% or less of second power or a second amount of power that is supplied to the power supply in a case where the measurement value is lower than the first threshold.

9. The power supply unit according to claim 1, further comprising:
   a charger configured to convert power which is input, into charging power for the power supply,
   wherein, among the charger and the control device, only the control device includes the temperature measuring unit.

10. The power supply unit according to claim 9, wherein the control device performs control on switching between a state where the temperature of the power supply is acquirable and a state where the temperature of the power supply is not acquirable.

11. A power supply unit for an aerosol inhaler, the power supply unit comprising:
   a power supply able to discharge power to a load for generating an aerosol from an aerosol generation source;
   a discharging terminal configured to connect the load to the power supply;
   a charging terminal configured to connect the power supply to an external power supply and to be separate from the discharging terminal;
   a temperature measuring unit configured to measure temperature of the power supply; and
   a control device configured to control an effective value of a first charging current to a value smaller than an effective value of a second charging current, wherein the first charging current is supplied to the power supply in a case where a measurement value of the temperature measuring unit is equal to or higher than a first threshold and the second charging current is supplied to the power supply in a case where the measurement value is lower than the first threshold, wherein
   in a case where the measurement value is equal to or higher than a second threshold larger than the first threshold, the control device stops charging of the power supply, and
   a value which is obtained by subtracting the first threshold from the second threshold is equal to or larger than an absolute value of an error of the temperature measuring unit in measuring the temperature.

12. A power supply unit for an aerosol inhaler, the power supply unit comprising:
   a power supply able to discharge power to a load for generating an aerosol from an aerosol generation source;
   a discharging terminal configured to connect the load to the power supply;
   a charging terminal configured to connect the power supply to an external power supply and to be separate from the discharging terminal;
   a temperature measuring unit configured to measure temperature of the power supply;
   a control device configured to control an effective value of a first charging current to a value different from an effective value of a second charging current, wherein the first charging current is supplied to the power supply in a case where a measurement value of the temperature measuring unit is equal to or higher than a first threshold and the second charging current is supplied to the power supply in a case where the measurement value is lower than the first threshold;

a charger configured to convert power, which is input from the charging terminal, into charging power for the power supply, wherein the charger includes an information input part and is configured to be able to change an effective value of a charging current that is supplied to the power supply based on an input which is input from the information input part, among the charger and the control device, only the control device acquires the temperature measured by the temperature measuring unit, and the control device changes inputs to the information input part based on the temperature to control the effective value of the charging current that is supplied to the power supply.

* * * * *